United States Patent [19]

Bannard et al.

[11] Patent Number: 5,071,877

[45] Date of Patent: Dec. 10, 1991

[54] METAL OXIMATE/POLYETHYLENE GLYCOLS CHEMICALS DECONTAMINANT SYSTEM

[76] Inventors: Robert A. B. Bannard, 38 Robertlee Drive, Carp, Ontario K0A 1L0; Alfred A. Casselman, General Delivery, Greely, Ontario, both of Canada; J. Garfield Purdon, 12 Calder Green S. E., Medicine Hat, Alberta, Canada, T1B3K6

[21] Appl. No.: 364,671

[22] Filed: Apr. 11, 1989

Related U.S. Application Data

[63] Continuation-in-part of Ser. No. 259,978, Oct. 5, 1988, abandoned, which is a continuation of Ser. No. 26,396, Feb. 24, 1987, abandoned.

[30] Foreign Application Priority Data

Oct. 24, 1986 [CA] Canada .................................. 521284

[51] Int. Cl.$^5$ .............................................. A61K 7/42
[52] U.S. Cl. .................................... 514/640; 514/731; 514/887
[58] Field of Search .................... 514/640, 731, 887

[56] References Cited

U.S. PATENT DOCUMENTS

| | | | |
|---|---|---|---|
| 4,081,552 | 3/1978 | Welle et al. | 514/640 X |
| 4,376,763 | 3/1983 | Barth et al. | 424/49 |
| 4,424,378 | 1/1984 | Mookherjee et al. | 424/70 X |
| 4,444,570 | 4/1984 | Barth et al. | 424/49 X |
| 4,522,808 | 6/1985 | Jacquet et al. | 424/70 X |
| 4,576,740 | 3/1986 | Hall et al. | 424/70 X |
| 4,663,152 | 5/1987 | Barth et al. | 424/49 |
| 4,816,487 | 3/1989 | Schewe et al. | 514/640 X |
| 4,879,106 | 11/1989 | Voli | 424/640 X |

Primary Examiner—Peter A. Nelson
Attorney, Agent, or Firm—Nixon & Vanderhye

[57] ABSTRACT

A cream or lotion consisting essentially of at least one active ingredient chosen from the alkali metal salts of certain oximes, phenols or polyethylene glycol monoethers, dispersed in a substantially anhydrous state in a base medium comprising of polyethylene glycol(s) which has (have) optionally been at least partially etherified to reduce the free hydroxyl group content thereof. These creams or lotions are effective against chemical warfare agents of both the V and G types, and against mustard gas (H or HD), and are simpler to make than known potassium salt-containing creams, for example those containing a macrocyclic ether and/or inert thickener and potassium phenate. These creams or lotions may be used both for protection and decontamination, and some may be used as personal barrier creams.

30 Claims, No Drawings

METAL OXIMATE/POLYETHYLENE GLYCOLS CHEMICALS DECONTAMINANT SYSTEM

CROSS-REFERENCE TO RELATED APPLICATION

This application is a continuation-in-part of earlier application Ser. No. 07/259,978 filed Oct. 5, 1988, now abandoned, which is a continuation of application Ser. No. 07/026,396, filed Feb. 24, 1987, now abandoned.

This invention relates to a decontaminant cream or lotion formulation which can be used to remove chemical warfare agents from exposed areas. Certain of these creams can also be used as protective barrier creams on exposed areas, including barrier creams for personal use.

BACKGROUND OF THE INVENTION

The types of chemical warfare agents which are considered to constitute a major threat are those commonly designated as HD, V and G. The first of these, HD, is an acronym for mustard gas, the 'D' implying that it is distilled. The formula for this compound is $ClCH_2CH_2-S-CH_2CH_2Cl$. It belongs to the vesicant class of chemical warfare agents. V and G stand for the V- and G-series of nerve agents. The G-series tend to be volatile and highly toxic by inhalation, whilst the V-agents are relatively non-volatile, persistent, and highly toxic by the percutaneous route.

Typical examples of these series are GD and VX which have the following formulae:

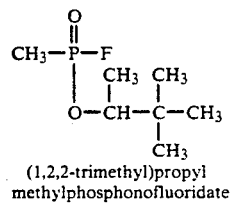

(1,2,2-trimethyl)propyl methylphosphonofluoridate

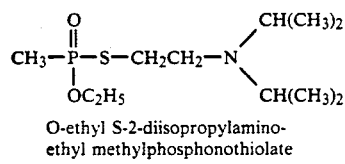

O-ethyl S-2-diisopropylamino-ethyl methylphosphonothiolate

To be of practical use under field conditions, any cream or lotion which is to be used either for decontamination or as a cream providing protection against chemical warfare agents has to possess certain desirable properties. First, it must be effective against all three of these types of chemical warfare agents. Second, for use as a barrier cream, it must be compatible with human skin and not cause any adverse reactions, at least over a limited period of time. Third, it must provide protection for a reasonable period of time. In this context it is to be noted that "decontamination" includes both coating before exposure to negate effects, and cleaning after exposure to remove potentially lethal deposits. These three criteria effectively exclude many of the currently known decontamination systems which have been devised as a means of destroying chemical warfare agents either for use as barrier creams, or to decontaminate relatively sensitive substances such as fabrics and the like. The chief difficulty is that such decontamination systems contain very powerful reagents which often will damage the surface being treated. Some of these systems are very alkaline, and some use concentrated active chlorine or bleach solutions. Thus, although these systems are, more or less, efficacious as decontaminants for equipment which has been exposed to chemical warfare agents, they are of no use in protecting or decontaminating people, and give no guide at all as to the sort of systems that might be used to formulate protective systems.

One solution to the barrier cream problem has been proposed which permits the formulation of a cream which is effective against all three types of agents, causes minimal adverse skin reactions during the periods of time for which such a barrier cream is likely to be worn, and also provides the wearer with protection for a reasonable period of time.

Although these proposed creams contain a reagent that is potentially extremely basic, for example, potassium phenoxide, they do appear to be compatible with skin.

In detail, these proposed creams provide a barrier cream consisting essentially of at least one active ingredient chosen from the alkali metal salts of mono- and dihydroxy phenols, and alkyl and mono alkoxy substituted mono and dihydroxy phenols, in which the alkyl groups each contain from 1 to 4 carbon atoms, dispersed in a substantially anhydrous state in a base medium comprising a polyethylene glycol which has been partially etherified to reduce the free hydroxyl group content. In these creams the preferred active ingredient is potassium phenoxide.

Similar creams have also been proposed in which the active ingredient is chosen from an alkali metal, preferably potassium, salt of phenol, acetophenone oxime, acetone oxime and 2,3-butanedione monoxime, together with a similar polyethylene glycol base, which also includes a macrocycle chosen from the compounds known as 18-crown-6 and crypt and[2,2,2], and a small amount of water.

Whilst these creams have been found to be effective, in that they meet the three main properties enumerated above reasonably efficiently, they are not without certain disadvantages, for example the macrocycles used are expensive.

These creams contain essentially three components: the reactive substance, which destroys the chemical warfare agent, a macrocycle and the base in which they are dispersed. To prepare these creams, the reactive substance, for example potassium phenoxide and macrocycle have to be prepared first, and then added to the base. These substances are both difficult to prepare and difficult to handle since they are particularly sensitive to reaction with water.

An advantage would be gained, therefore, if the preparation of these creams could be simplified.

DETAILED DESCRIPTION OF THE INVENTION

We have now discovered that such a cream or lotion can be prepared both simply and easily, by dispersing the active ingredient (the alkali metal salt, for example the potassium salt) directly into the same sort of polyethylene glycol ether as is used to provide the major part of the cream base in the creams proposed above. In one particular, and special, case, the active substance can be prepared directly in the polyethylene glycol base, by reacting a suitable polyethylene glycol with an alkali metal, especially potassium.

Thus in its broadest aspect this invention provides a cream or lotion consisting essentially of at least one active ingredient chosen from the alkali metal salts of mono- and di-hydroxy phenols; alkyl and mono-alkoxy substituted mono- and di-hydroxy phenols, in which the alkyl groups each contain from 1 to 4 carbon atoms; acetophenone oxime; 2,3-butanedione monoxime, or a polyethylene glycol monoether, as active component dispersed in a substantially anhydrous state in a base medium comprising a polyethylene glycol which has been at least partially etherified to reduce the free hydroxyl group content thereof.

Preferably the polyethylene glycol base medium has the general formula.

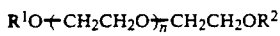

in which $R^1$ and $R^2$ each independently represent hydrogen or an alkyl group, and n is an integer of at least 1.

The potassium salts used in these creams generally are prepared separately, in a relatively pure state. Whilst separate preparation of the salt has the advantage that the salt can then be identified and, if desired, purified, it has the disadvantage mentioned above for the creams containing, for example, potassium phenate, that these salts require careful handling in dry conditions. In one particular instance what may be called a "one-pot" technique may be used whereby the salt is prepared in situ directly. This method is particularly advantageous since it both minimizes the handling of sensitive compounds, and simplifies cream or lotion preparation.

It is somewhat surprising that these salts can be prepared by direct reaction of the alkali metal with a monomethyl polyethylene glycol. Other workers have suggested that alkoxides cannot be prepared directly from polyethylene glycols and alkali metals, and recommended the use of an intermediate, for example sodium naphthide. It has been reported, however, that sodium metal will react with a polyethylene glycol having a molecular weight of about 4000. Our investigations show that an alkali metal salt is being prepared, for example we have isolated and characterized (by means of elemental analysis, IR and NMR investigations) the potassium salt of diethylene glycol monomethyl ether, $CH_3—O—CH_2CH_2—O—CH_2CH_2—OK$.

When the one-pot method is used, the choice of polyethylene glycol both as reactant and as cream or lotion base -which is also present- is quite broad, and is generally similar to those used directly as a cream or lotion base.

The polyethylene glycol used as the reactant generally will have the formula

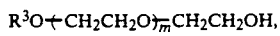

in which $R^3$ is an alkyl group, usually of 1–4 carbon atoms, and especially methyl or ethyl. The value of m can be quite broad, ranging from ](i.e., a diethylene glycol mono-ether) up to at least about 50, to give a polyethylene glycol with a molecular weight of about 1900. It is also contemplated to use a mixture of polyethylene glycol ethers, for example, both to give a reasonable reaction rate and a reasonable cream or lotion consistency. Alternatively, the alkali metal salt can be prepared directly in a mixture of a polyethylene glycol monoether in a diether, for example a mixture of diethylene glycol monomethyl ether in "tetraglyme", which has the formula

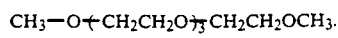

In selecting the blend of polyethylene glycols and ethers to be used in the creams and lotions of this invention, apart from ensuring that there is enough hydroxyl group content to provide an adequate concentration of alkali metal salt (it is to be remembered that for the mono-ethers as the molecular weight increases, hydroxyl content decreases) two factors have to be balanced. Ideally, the final cream or lotion should be free of any excess of hydroxyl groups in order to be able to utilize fully the destructive powers against the chemical warfare agents of the active alkali metal salts. This suggests that the base material should be diethers. Experience shows, however, that the salts are not too soluble in such systems, and hence generally a mix of diether and at least some mono-ether is required in order to achieve a balance of properties. In those applications in which maximum capacity for dissolution of active ingredient is desirable and the rate of destruction is not as critical, use of non-etherified polyethylene glycols may be warranted.

The base medium used in these creams and lotions can be chosen from a wide range of compounds, and indeed need not be a single compound at all. The chief requirement is that it provides an adequate cream or lotion consistency. The polyethylene glycols being considered here have the general formula $R^1O(CH_2CH_2O)_nCH_2CH_2OR^2$, in which both $R^1$ and $R^2$ are hydrogen. For the creams and lotions of this invention intended for use on skin, the hydroxyl groups need to be etherified, at least in part. Thus, for skin application generally at least one of $R^1$ and $R^2$ will not be hydrogen. Suitable etherifying groups are alkyl groups of up to 4 carbon atoms. Typically the etherifying groups will be methyl or ethyl groups. It is thus apparent that a suitable base medium can be obtained either by etherifying a mixture of polyethylene glycols, mixing pre-etherified polyethylene glycols, or by mixing together a fully etherified polyethylene glycol with a suitable amount of a second unetherified or mono-etherified polyethylene glycol, which may be a polyethylene glycol of different chain length to the etherified one. For applications other than to skin, the polyethylene glycols being considered for creams or lotions of this invention have the general formula $R^1O—(CH_2CH_2O)_n—CH_2CH_2—OR^2$, in which $R^1$ and $R^2$ may each be hydrogen or an alkyl group of up to 4 carbon atoms. The particular formulation of base medium will be dictated by the specific applications.

The value of n in the above formulae can be chosen from a wide range. If n is high enough, for example, to give a molecular weight above 750 or so, then the polyethylene glycol ether will itself provide the required consistency for the cream or lotion. Alternatively, if n is small, for example, the compound

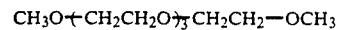

known as "tetraglyme", then the polyethylene glycol ether is a liquid and cannot provide a cream by itself. It may be thickened by adding to it any of the substances commonly used in pharmaceutical creams for this purpose, such as silicas, titania, Fuller's earth, clays, bentonite, and so forth. The filler used also has to be one which will not react with the active ingredient. Thus an "active" silica may need to be etherified before use.

The creams and lotions of this invention also proffer a further unexpected advantage. It was noted above that the equipment decontamination systems commonly used cannot be used on skin due to their chemical nature. This also means that such systems tend to be of questionable use for decontaminating porous equipment surfaces such as fabrics and webbing. If these chemical solutions are left in contact with such porous materials long enough to penetrate them adequately, then they are also likely to damage the materials as well. This appears not to be the case with certain of the creams of this invention, particularly those incorporating phenoxide and oximate salts, which can be left in contact with porous contaminated surfaces for extended periods of time without any damage resulting. It is noted above that certain creams of this invention which again contain phenoxide and certain oximate salts do not affect the skin.

EXAMPLE 1

Preparation of the Potassium Salt of Diethylene glycol monomethyl Ether

Method I

Metallic potassium ($\approx 2.5$ g, $6.4 \times 10^{-2}$ gram atom, accurately weighed) was placed in a nitrogen-flushed, 2L round-bottom, three-neck flask containing 150 mL of hexane (sodium dried) and equipped with a magnetic stirring bar. The flask was also fitted with a condenser, nitrogen inlet tube and pressure-equalizing dropping funnel, each separated from the flask by a large-bore stopcock which allowed for isolation of the flask and reaction product from the remainder of the apparatus. The apparatus was protected from moisture and carbon dioxide and fitted with an exit bubbler to monitor the nitrogen flow (250 mL per minute). A solution containing a ten percent excess (8.46 g, $7.04 \times 10^{-2}$ mole) of diethylene glycol monomethyl ether (2-glycol MME, dried over activated molecular sieves) in 20 mL of cyclohexane (sodium dried) had been placed in the dropping funnel (in a dry-lab, argon atmosphere) prior to assembling the apparatus. The potassium-hexane mixture was heated with stirring under reflux to disperse the potassium. The 2-glycol MME-cyclohexane solution was then added dropwise over approximately fifty minutes. The reaction was continued under reflux for six to seven hours, after which heat was removed while the nitrogen flow was maintained to avoid intake of air. The cooled flask containing the product was isolated from the rest of the apparatus via the stopcocks and transferred to a dry-lab for workup. The precipitate which separated on cooling was collected and washed with hexane (sodium dried) followed by ether (sodium dried) and provided the potassium salt of 2-glycol MME as colorless crystals. Yield 6.98 g, 69%, m.p. 89°-91° C. Anal. Calcd. for $C_5H_{11}O_3K$. C,37.95; H,7.01; K, 24.71. Found: C,37.70, 37.67; H, 7.03, 6.99; K, 24.45, 24.56%.

Method II

Method I was modified by substituting tetraethylene glycol dimethyl ether (chromatographed through both basic and acidic alumina, dried over molecular sieves), 50 mL for the hexane. The reaction was conducted using 0.387 g ($9.9 \times 10^{-3}$ gram atom) of potassium and 1.82 g ($1.5 \times 10^{-2}$ mole) of 2-glycol MME (50% excess) at 65°-70° C. The 2-glycol MME was added dropwise in tetraglyme (20 mL) over 15 minutes and heating was continued for three hours. Potassium-2-glycol MME was not isolated but was made up to 0.1M concentration with tetraglyme and screened for reactivity against HD, GD and VX. See Table IV for results.

Carbon-13 NMR and proton NMR spectra of K-2-glycol MME were recorded on a Varian XL-200 FT NMR Spectrometer using a solution containing 0.03 g of salt in 0.5 mL of dimethyl sulfoxide-$d_6$ (DMSO-$d_6$), unless otherwise stated. Infrared spectra were recorded on a Perkin-Elmer Infrared Spectrophotmeter Model 283.

EXAMPLE 2

Potassium Salt of Polyethylene Glycol Monomethyl Ether, Molecular Weight 350 (PEGMME 350)

The preparation was performed in a dry-lab in an argon atmosphere. Potassium (0.0979 g, $2.5 \times 10^{-3}$ gram atom) and PEGMME 350 (dried over molecular sieves), 12 mL, were placed in a 25 mL round-bottom flask equipped with a magnetic stirrer and heated at 65°-70° C. for four hours. The product, (potassium-PEGMME 350) was not isolated but was made up to known concentration (0.5 or 0.1M) with PEGMME 350 and examined for reactivity vs VX. For comparison, the salt isolated from Method I above was also made up to 0.1M in PEGMME 350 and tested against VX. See Table V for results.

EXAMPLE 3

Potassium Salt of a Barrier Cream Base

The preparation was performed in a dry-lab in an argon atmosphere. Sixty mL of a base cream (50% PEGMME 550 and 50% PEGMME 1900, W:W %) melt which had been dried at $10^{-3}$ Torr for 3h and potassium (1.12 g, 0.029 gram atom) were placed in a 200 mL round-bottom flask equipped with a magnetic stirrer and heated at 65°-70° C. for four hours and forty minutes. The resulting solution, when cooled, produced a homogeneous cream with excellent texture and spreading qualities.

EXAMPLE 4

Screening: Decontaminants vs CW Agents

The CW agent solutions were prepared by weighing 0.4 milliequivalents (i.e. HD, 31.8 mg; VX, 106.8 mg; GD, 72.8 mg) of a given agent into 1 mL volumetric flasks and making up to volume with the same solvent in which the candidate decontaminant salt was dissolved (See Tables I, IV, V). For screening, an aliquot (25 µL) of the agent solution was transferred via a microliter syringe to a 3 mL Reacti-Vial TM (Pierce Chemical Co) equipped with a teflon-lined silicon rubber septum and a triangular magnetic stirrer. The candidate decontaminant solution (400 µL) was added to the Reacti-Vial via a microliter syringe and the resultant solution was stirred at 19°-22°. The ratio of salt:agent was adjusted by altering the concentration of the salt solution. See Tables IV and V for these ratios, salt concentrations, solvents used and reaction times. At the end of the selected reaction times the systems were quenched with a twenty-five-fold excess (relative to the nucleophile salt) of glacial acetic acid.

The extent of decontamination achieved was obtained from agent destruction as determined by gas chromatographic analysis using an external agent standard. The standard was prepared in the same solvent as that used in the decontamination experiment at a concentration equal to that initially present in the reaction mixture. Injections (1 μL) of the standard were made before and after those from the decontamination experiments and by comparison of the peak areas the amount of agent destruction was calculated.

A Perkin-Elmer gas chromatograph (GC) Model Sigma 1B, equipped with a thermal conductivity detector (TCD) and dedicated computer, complete with recorder, for data manipulation was used for all GC analysis. The TCD and injection port were maintained at 250° and 240° respectively. The injection sample size was 1 μL. The instrument was fitted with a 10ft×2mm I.D. column and a 6 in. precolumn, both constructed of silanized glass and both packed with 10% UCW-98 on Gas Chrom Q ™, 80/100 mesh. All other GC parameters are shown in Table I.

EXAMPLE 5

Cream Preparations

The selected active ingredient salt is weighed (taking suitable precautions: i.e., in a dry box and in an inert atmosphere) into an appropriately sized jar fitted with a polytetrafluoroethylene lined cap. The weighed salt, in its jar, the base cream and a large syringe are then equilibrated in an oven at 55° C., in order primarily to render the cream adequately fluid. The required amount of cream is then transferred to the jar which is then stirred to disperse the salt evenly into the liquified cream. This can require several hours stirring (for example with a magnetic stirrer using a small bar in the jar) at a temperature in the 50°–60° C. range. Thereafter the creams are allowed to cool, stirred to a smooth texture with a spatula, and transferred to suitable sealed containers in a dry box.

The following creams were prepared by this route, using the following four base creams (it is to be noted that the numbers following PEG indicate an approximate average molecular weight: e.g., PEG 350 is a polyethylene glycol which has an approximate molecular weight of 350; percentages are given by weight).

| Base Cream: | 1. | 50% PEG | 1900 monomethylether |
|---|---|---|---|
| | 2. | 50% PEG | 550 monomethylether |
| | | 50% PEG | 1900 monomethylether |
| | 3. | 60% PEG | 600 |
| | | 40% PEG | 1900 monomethylether |
| | 4. | 40% PEG | 550 monomethylether |
| | | 60% PEG | 1900 monomethylether |

Using these bases, creams were prepared containing potassium phenoxide, potassium 2,3-butanedione monoximate, potassium acetophenone oximate, and potassium acetone oximate at a concentration of 1.25 molar. In each case, for bases 1 and 2 at least about 75% of the salt appears to dissolve, the remainder being finely dispersed. Using base 3, the salt appears to dissolve completely. Base 4 was used only with potassium acetophenone oximate, which appears to be soluble in this base.

EXAMPLE 6

Cream Evaluation

Test Species—Albino male guinea pigs (approx 500 g), virus-free Hartley strain, were obtained and were acclimatized for at least one week before use.

Challenge Procedure—An area 80 cm$^2$ on the back of each animal was shaved and treated with hair remover to provide a depilated test surface. The following morning, the animals were weighed and placed on a restraining tray which permitted head movement and eating from the front of the tray but did not permit sufficient torso movement to endanger the test area on the back. A 3×4 cm area was marked on the depilated back skin and a measured volume of cream, 0.8 mL, was spread evenly over the marked zone. This produced a layer 0.5–0.6 mm thick. One hour following application of the cream, droplets of chemical warfare agent were applied to the surface of the cream at separated locations until the total dose desired had been administered. The restrained animals were placed in a fume hood facing the air flow to minimize the possibility of inhaling the agent vapour. After 6h they were freed, transferred to small individual wire cages and kept overnight. Fresh lettuce and carrots were provided during the period of restraint and food and water were provided to the caged animals. All animals were examined regularly during the restraint period for clinical signs. If death occurred, the time of death was recorded. Twenty-four hours following application of the agent, the cream was carefully washed from backs of the surviving animals and the area of application was examined for skin damage. Surviving animals were examined for other physiological abnormalities and euthanized with carbon dioxide. If abnormal tissues were found at necropsy, samples were collected for biological examination.

Each group of experimental animals included at least 2 which were treated with agent in the absence of cream (agent controls). At least 4 were treated with agent following the application of base cream containing no active ingredient (cream control). At least 10 were treated with agent following the application of active cream.

With nerve agents, group statistics generated included average time of death, percent survival, body weight, dose of agent and tissue examination data.

With mustard (HD) a modified Draize scoring system was used similar to that described elsewhere, but was expressed as percent protection provided by base or active cream in relation to the skin damage caused to untreated controls

Doses of Agent Applied

1. Mustard (HD): 0.4, 0.8, 1.2 and 1.6 μL/12 cm$^2$
2. GD in 4 μL and fraction thereof droplet size
  (a) Barrier cream: 16 LD$_{50}$
  (b) Base cream: 8 LD$_{50}$
3. VX in 4 μL and fraction thereof droplet size
  (a) Barrier cream: 68 LD$_{50}$
  (b) Base cream: 34 LD$_{50}$

Active Ingredients

1. Potassium phenoxide (KOPh)
2. Potassium 2,3 butanedione monoximate (KDAMO)
3. Potassium acetophenone oximate (KOMP)

Cream Formulations tating to eyes. The other creams were not tested for skin or eye irritancy.

TABLE I

Gas Chromatographic Parameters for Analysis of CW Agents

| Agent | Solvent | Carrier gas (He) flow rate (mL/min) | Oven Temp lower (°C.) | Lower hold (min) | Program rate (°C./min) | Oven Temp upper (°C.) | Upper hold (min) | Agent retention time (min) |
|---|---|---|---|---|---|---|---|---|
| HD[a] | Tetraglyme | 20 | 100 | 0 | 5 | 150 | 0 | 8.0 |
| HD[b] | | | 150 | 0 | 40 | 230 | 5 | |
| GD | Tetraglyme | 20 | 95 | 15 | 40 | 230 | 5 | 8.6 |
| VX | Tetraglyme | 30 | 200 | 5 | 35 | 235 | 5 | 5.1 |
| VX | 2-Glycol MME | 30 | 200 | 5 | 35 | 235 | 5 | 4.9 |
| VX[a] | PEG MME 350 | 30 | 200 | 5 | 35 | 235 | 5 | 5.3 |
| VX[b] | | | 235 | 5 | 35 | 250 | 45 | |

[a]First stage in temperature program.
[b]Second stage in temperature program.

These were prepared as described in Example 5. For convenience in tabulation of results and in discussion the following designations are used.

MG1 - Base Cream 1.
MG2 - Base Cream 2.
MG3 - Base Cream 3.
MG4 - Base Cream 4.
PMG1 (1.25 m KOPh) - 1.25 molal KOPh, in Base Cream #1
PMG2 (1.25 m KOPh) - 1.25 molal KOPh, in Base Cream #2
PMG3 (1.25 m KOPh) - 1.25 molal KOPh, in Base Cream #3
PMG2 (1.0 m KOPh) - 1.0 molal KOPh, in Base Cream #2
PMG2 (1.5 m KOPh) - 1.5 molal KOPh, in Base Cream #2
PMG2 (2.0 m KOPh) - 2.0 molal KOPh, in Base Cream #2
OMG2 (1.25 m KDAMO) - 1.25 molal KDAMO, in Base Cream #2
OMG2 (1.25 m KOMP) - 1.25 molal KOMP, in Base Cream #2
OMG4 (1.25 m KOMP) - 1.25 molal KOMP, in Base Cream #4

A subjective assessment was made of the cosmetic characteristics (appearance, color, spreading and integrity), of the creams and of their irritancy to both skin and eyes.

Results

The base creams MG2 and MG4 provided significant levels of protection against HD when challenged at the same dosage level as used on the active creams (Table VI). On the other hand, they provided only erratic protection against GD and none against VX when challenged with half the normal dose used for the active creams.

All the active creams provided high levels of protection against all three agents demonstrating excellent performance and reproducibility, except for PMG2 (1.25 m KOPh) in the case of VX and for OMG4 (1.25m KOMP) in the case of GD.

The cosmetic characteristics of the MG2-based systems were judged to be slightly superior to those of the MG1-based and MG3-based systems, which were slightly softer and harder, respectively (Table VIII). It is possible that these slight differences could have been corrected by minor adjustments to the proportions of the PEG components.

Base creams MG2 and MG4 and active creams PMG2 (1.25 m KOPh) and OMG2 (1.25 m KDAMO) were non-irritating to guinea pig skin (24h applications under ventilated or occluded conditions) and to rabbit eyes. Active cream OMG4 (1.25 m KOMP) on the other hand, was slightly irritating to skin and very irri-

TABLE II

Proton NMR Spectrum of K-2-glycol MME[a]

| Compound | $CH_3$—O—$CH_2$—$CH_2$—O—$CH_2$—$CH_2$—OK | | | |
|---|---|---|---|---|
| Proton label | | | A | |
| Chemical shift (ppm)[b] | 3.28 | 3.48 | 3.33 | 3.96 |
| Type of peak | singlet | singlet | singlet | triplet |
| Integration | 3[c] | 4[c] | 2[c] | 2[c] |

[a]K-2-glycol MME = potassium salt of diethylene glycol monomethyl ether.
[b]Downfield from trimethylsilane.
[c]Number of hydrogens.

TABLE III

Chemical Shifts in the Proton NMR of the K-Salt-2-Glycol MME[a] at Various Concentrations

| Proton label[b] | A | B | C | D |
|---|---|---|---|---|
| Type of Signal | Singlet | Singlet | Triplet | Triplet |
| Concentration (g per 0.5 mL) (DMSO-$d_6$) | Chemical shift (ppm) | | | |
| 0.0062 | 3.27 | 3.46 | 3.32 | 3.85 |
| 0.0106 | 3.27 | 3.47 | 3.33 | 3.91 |
| 0.0208 | 3.27 | 3.47 | 3.34 | 3.93 |
| 0.0304 | 3.28 | 3.48 | 3.33 | 3.96 |
| 0.0459 | 3.28 | 3.48 | 3.33 | 3.96 |

[a]K-2-glycol MME = potassium salt of diethylene glycol monomethyl ether.
[b]See Table II for label identification.
[c]Downfield from trimethylsilane.

TABLE IV

Decontamination Efficiency of K-2-Glycol MME in Tetraglyme against HD, VX, and GD

| Preparation method | CW agent | Ratio salt:agent | Salt conc (M) | % Decontamination at reaction time | | | | |
|---|---|---|---|---|---|---|---|---|
| | | | | 5 min | 3 min | 1 min | 30 sec | 10 sec |
| I | HD | 2:1 | 0.05 | — | — | 100 | 100 | 99 |
| | HD | 1:1 | 0.025 | — | 96 | 91 | — | 75 |
| | VX | 2:1 | 0.05 | — | — | — | 100 | 100 |
| | VX | 1:1 | 0.025 | 87 | — | 80 | 67 | — |
| | GD | 2:1 | 0.05 | — | — | 100 | 100 | 100 |
| | GD | 1:1 | 0.025 | — | 93 | 91 | 88 | 67 |
| II | HD | 2:1 | 0.05 | 100 | 100 | 100 | 99 | 87 |
| | HD | 1:1 | 0.025 | 94 | 89 | 82 | 92 | 85 |
| | VX | 2:1 | 0.05 | — | 100 | — | 100 | 100 |
| | VX | 1:1 | 0.025 | — | — | 100 | 100 | 98 |
| | GD | 2:1 | 0.05 | — | — | — | 100 | 100 |
| | GD | 1:1 | 0.025 | 80 | 77 | 82 | 78 | — |

I = salt prepared in hexane/cyclohexane isolated and identified.
II = salt prepared in situ in tetraglyme.

TABLE V

Decontamination Efficiency of Potassium Salts of 2-Glycol MME and PEG 350 MME against VX

| Experiment No. | Ratio salt:agent | Concentration of salt (M) | Solvent | % Decontamination at reaction time | | | | | | |
|---|---|---|---|---|---|---|---|---|---|---|
| | | | | 10 S | 30 S | 1 M | 5 M | 10 M | 15 M | 20 M |
| 1[a,b] | 2:1 | 0.05 | tetraglyme | 100 | 100 | — | — | — | — | — |
| 2[a] | 4:1 | 0.1 | 2-Glycol MME[d] | — | — | 7 | 19 | 36 | 48 | 54 |
| 3[a] | 4:1 | 0.1 | PEGMME 350[e] | — | — | 33 | 56 | 73 | 88 | 96 |
| 4[c] | 4:1 | 0.1 | PEGMME 350 | — | — | 33 | 53 | 72 | 89 | 97 |
| 5[c] | 20:1 | 0.5 | PEGMME 350 | 46 | 100 | 100 | 100 | 100 | — | — |

[a]Potassium salt of diethylene glycol monomethyl ether.
[b]Data extracted from Table IV.
[c]Potassium salt of polyethylene glycol monomethyl ether, molecular weight 350.
[d]2-Glycol MME = diethylene glycol monomethyl ether.
[e]PEGMME 350 = polyethylene glycol monomethyl ether, molecular weight 350.

TABLE VI

Protection[1] Provided to Male Guinea Pigs by Active and Base Creams Against HD, VX, and GD

| | Cream | Agent | | |
|---|---|---|---|---|
| | | HD | GD | VX |
| Base | MG2 | 77 ± 6 (26) | 43 ± 31 (15)[2] | 0 (13)[2] |
| | MG4 | 76, 91 (2) | 0, 25 (2) | 0 (3) |
| Active | PMG2 (1.25 m KOPh) | 91 ± 8 (6)[3] | 98 ± 4 (8) | 66 ± 21 (10) |
| | OMG2 (1.25 m KDAMO) | 92 ± 4 (6) | 96 ± 4 (5) | 98 ± 4 (4) |
| | OMG2 (1.25 m KOMP) | 95 ± 4 (9) | 98 ± 4 (5) | 96 ± 4 (7) |
| | OMG4 (1.25 m KOMP) | 98 ± 2 (3) | 60, 100 (2) | 90, 100 (2) |

[1]Protection = % survival for GD and VX and % reduction in total skin damage effects (modified Draize) in relation to unprotected controls for HD.
[2]Note that agent challenges for GD and VX on base creams were only half those on active creams, 8 $LD_{50}$ and 34 $LD_{50}$ respectively, rather than 16 $LD_{50}$ and 68 $LD_{50}$. A full challenge of HD was used.
[3]Values in parentheses for active creams indicate numbers of experiments conducted using at least 10 animals per experiment.

TABLE VII

Effect of KOPh Concentration on Protection[1] Provided to Male Guinea Pigs by PMG Barrier Creams

| | % Protection Range vs VX | |
|---|---|---|
| Cream | Barrier | Base |
| PMG2 (1 m) | 0,50 (2)[2] | 0 (2) |
| PMG2 (1.25 m) | 75,90 (2) | 0 (2) |
| PMG2 (1.5 m) | 40,100,90 (3) | 0 (3) |
| PMG2 (2 m) | 62,90 (2) | 0 (2) |

[1]Protection = % Survival
[2]Values in parentheses for active creams indicate number of experiments conducted using 10 animals per experiment.

TABLE VIII

Cosmetic Characteristics and Irritancy of Base Creams and Barrier Creams

| Cream | Color | Appearance | Hardness | Spreading quality | Integrity[1] | Irritancy[2] skin | eyes |
|---|---|---|---|---|---|---|---|
| MG1 | colorless | smooth | soft | good | good | * | * |
| MG2 | colorless | smooth | medium | very good | very good | — | — |
| MG3 | colorless | smooth | hard | poor | good | * | * |
| MG4 | colorless | smooth | medium | good | very good | — | — |
| PMG1 (1.25 m KOPh) | med. brown | smooth | soft | good | fair | * | * |
| PMG2 (1 m KOPh) | med. brown | smooth | medium | good | good | * | * |
| PMG2 (1.25 m KOPh) | med. brown | smooth | medium | very good | very good | — | — |
| PMG2 (1.5 m KOPh) | med. brown | smooth | medium | very good | very good | * | * |
| PMG2 (2 m KOPh) | med. brown | smooth | medium | good | good | * | * |
| PMG3 (1.25 m KOPh) | med. brown | smooth | hard | poor | good | * | * |
| OMG2 (1.25 m KDAMO) | orange | smooth | medium | very good | very good | — | — |
| OMG2 (1.25 m KOMP) | dark brown | smooth | soft | very good | fair | * | * |
| OMG4 (1.25 m KOMP) | dark brown | smooth | medium | very good | very good | + + | + + + + |

[1]24 h contact time
[2]Intact skin, 24 h contact time
— non irritating
+ barely visible irritation
+ + slight irritation
+ + + medium irritation
+ + + + severe irritation
* not tested The embodiments of the invention in which an exclusive property or privilege is claimed are defined as follows:

1. A cream or lotion for topical application to a person's skin as a decontaminant or barrier against chemical warfare agents, the cream or lotion compatible with human skin and consisting essentially of at least one active ingredient selected from the alkali metal salts of mono- and di-hydroxy phenols; alkyl and mono-alkoxy substituted mono- and di-hydroxy phenols, in which the alkyl groups each contain from 1 to 4 carbon atoms; acetophenone oxime; 2,3-butanedione monoxime, or a polyethylene glycol monoether, dispersed in a substantially anhydrous state in a base medium comprising a polyethylene glycol or mixture of polyethylene glycols which has/have been at least partially etherified to reduce the free hydroxyl group content thereof.

2. A cream or lotion according to claim 1 wherein the alkali metal is chosen from sodium and potassium.

3. A cream or lotion according to claim 2 wherein the alkali metal is potassium.

4. A cream or lotion according to claim 1 wherein the polyethylene glycol(s) base medium has/have the general formula

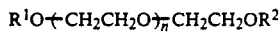

in which $R^1$ and $R^2$ each independently represent hydrogen or an alkyl group, and n is an integer of at least 1.

5. A cream or lotion according to claim 4 in which at least one of $R^1$ and $R^2$ is an alkyl group of up to 4 carbon atoms.

6. A cream or lotion according to claim 5 in which at least one of $R^1$ and $R^2$ is a methyl or ethyl group.

7. A cream or lotion according to claim 4 in which both $R^1$ and $R^2$ are methyl.

8. A cream or lotion according to claim 1 further including an inert powder thickener.

9. A cream or lotion according to claim 8 wherein the inert powder thickener is fine particle size silica.

10. A cream or lotion according to claim 1 wherein the polyethylene glycol base medium comprises a mixture of at least two polyethylene glycols, in which mixture at least one of the polyethylene glycols is etherified.

11. A cream or lotion according to claim 1 wherein the active ingredient is alkali metal salt of a polyethylene glycol monoether of the formula

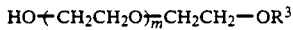

in which m is an integer of at least 1, and $R^3$ represents a lower alkyl group.

12. A cream or lotion according to claim 11 wherein $R^3$ represents a methyl or ethyl group.

13. A cream or lotion according to claim 12 wherein $R^3$ represents a methyl group.

14. A cream or lotion according to claim 11 wherein m is an integer of 1 to 50.

15. A cream or lotion according to claim 14 wherein m is chosen to provide a molecular weight of up to about 1900.

16. A cream or lotion according to claim 14 wherein m is chosen to provide a molecular weight of up to about 550.

17. A cream or lotion according to claim 14 wherein m is chosen to provide a molecular weight of up to about 350.

18. A cream or lotion according to claim 11 wherein $R^3$ is methyl and m is 1, to provide diethylene glycol monomethyl ether.

19. A cream or lotion according to claim 4 wherein n is chosen to provide a molecular weight of up to about 1900.

20. A cream or lotion according to claim 4 wherein n is chosen to provide a molecular weight of up to about 550.

21. A cream or lotion according to claim 4 wherein n is chosen to provide a molecular weight of up to about 350.

22. A cream or lotion according to claim 11 wherein the alkali metal is potassium.

23. A cream or lotion according to claim 1 wherein the active ingredient is an alkali metal salt of a mono- or di-hydroxy phenol; or an alkyl- or mono-alkoxy substituted mono- or di-hydroxy phenol, in which the alkyl groups each contain from 1 to 4 carbon atoms.

24. A cream or lotion according to claim 23 in which the active ingredient is an alkali metal salt of phenol.

25. A cream or lotion according to claim 24 in which the active ingredient is potassium phenoxide.

26. A cream or lotion according to claim 1 in which the active ingredient is an alkali metal salt of 2,3-butanedione monoximate.

27. A cream or lotion according to claim 26 in which the active ingredient is potassium 2,3-butanedione monoximate.

28. A cream or lotion according to claim 1 in which the active ingredient is an alkali metal salt of acetophenone oxime.

29. A cream or lotion according to claim 28 in which the active ingredient is potassium acetophenone oximate.

30. A cream or lotion consisting essentially of at least one active ingredient selected from the alkali metal salts of mono- or di-hydroxy phenols; alkyl and mono-alkoxy substituted mono- and di-hydroxy phenols, in which the alkyl groups each contain from 1 to 4 carbon atoms; acetophenone oxime; 2,3-butanedione monoxime, or a polyethylene glycol monoether, dispersed in a substantially anhydrous state in a base medium comprising a polyethylene glycol, a mixture of polyethylene glycols a polyethylene glycol ether, or a mixture of polyethylene glycols, which have been at least partially etherified to reduce the free hydroxyl group content thereof.

* * * * *

UNITED STATES PATENT AND TRADEMARK OFFICE
CERTIFICATE OF CORRECTION

PATENT NO. : 5,071,877

DATED : December 10, 1991

INVENTOR(S) : Bannard et al

It is certified that error appears in the above-identified patent and that said Letters Patent is hereby corrected as shown below:

Title Page, Item 76, Inventors, add the following inventor:

--Celso E. Mendoza of Medicine Hat, Canada--.

Signed and Sealed this

Twentieth Day of April, 1993

Attest:

MICHAEL K. KIRK

*Attesting Officer*    Acting Commissioner of Patents and Trademarks